(12) United States Patent
Lonky

(10) Patent No.: US 7,959,578 B2
(45) Date of Patent: Jun. 14, 2011

(54) METHODS AND TECHNIQUES TO MEASURE, MAP AND CORRELATE OCULAR MICRO-MOVEMENT AND OCULAR MICRO-TREMOR (OMT) SIGNALS WITH COGNITIVE PROCESSING CAPABILITIES IN ADD/ADHD INDIVIDUALS

(76) Inventor: Martin L. Lonky, Rancho Palos Verdes, CA (US)

( * ) Notice: Subject to any disclaimer, the term of this patent is extended or adjusted under 35 U.S.C. 154(b) by 0 days.

(21) Appl. No.: 12/362,046

(22) Filed: Jan. 29, 2009

(65) Prior Publication Data

US 2009/0198148 A1 Aug. 6, 2009

Related U.S. Application Data

(60) Provisional application No. 61/025,434, filed on Feb. 1, 2008.

(51) Int. Cl.
*A61B 13/00* (2006.01)
(52) U.S. Cl. .................................................. 600/558
(58) Field of Classification Search ............... 600/558, 600/595; 382/117; 606/4; 351/209
See application file for complete search history.

(56) References Cited

U.S. PATENT DOCUMENTS

| 6,231,187 B1 | 5/2001 | Munoz et al. |
| 6,652,458 B2 * | 11/2003 | Blazey et al. ............... 600/300 |
| 7,011,410 B2 | 3/2006 | Bolger et al. |
| 2006/0229505 A1 | 10/2006 | Mundt et al. |

OTHER PUBLICATIONS

International Search Report issued Apr. 6, 2009, pp. 1-2.

* cited by examiner

*Primary Examiner* — Max Hindenburg
*Assistant Examiner* — H. Q. Nguyen
(74) *Attorney, Agent, or Firm* — Sci-Law Strategies, PC

(57) ABSTRACT

An apparatus and method of collecting elements of and assembling various portions of ocular micro motions such as ocular micro-tremor (OMT) movements of the eye, and correlating them directly with OMT waveforms acquired from both known and unknown states of cognition and cognitive function. Comparing newly acquired waveforms from patients with undiagnosed cognitive dysfunctions, permits an individual or caregiver the ability to identify those unknown issues or cognitive states based on matching or relating statistically elements of their waveform with categories of other known cognitive processing normals and abnormals, functional and dysfunctional individuals. It also allows for measuring the effects of therapeutic agents (psychological or pharmacological) by relating them to measurable changes in cognitive function as a result of correlated changes in waveforms.

10 Claims, 13 Drawing Sheets

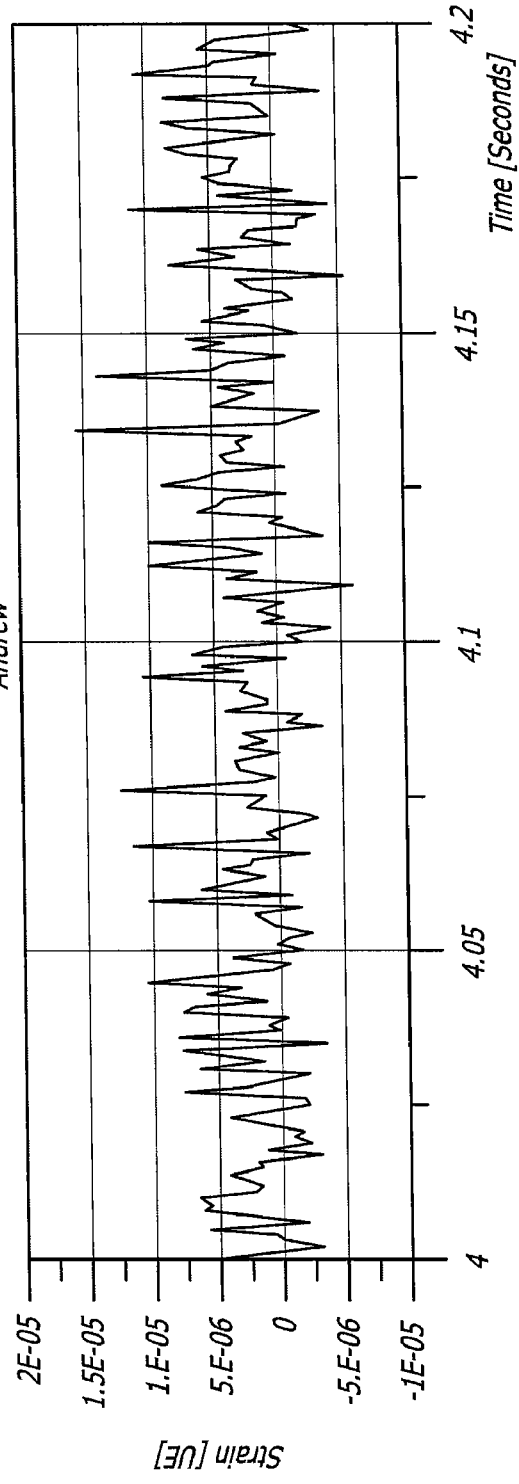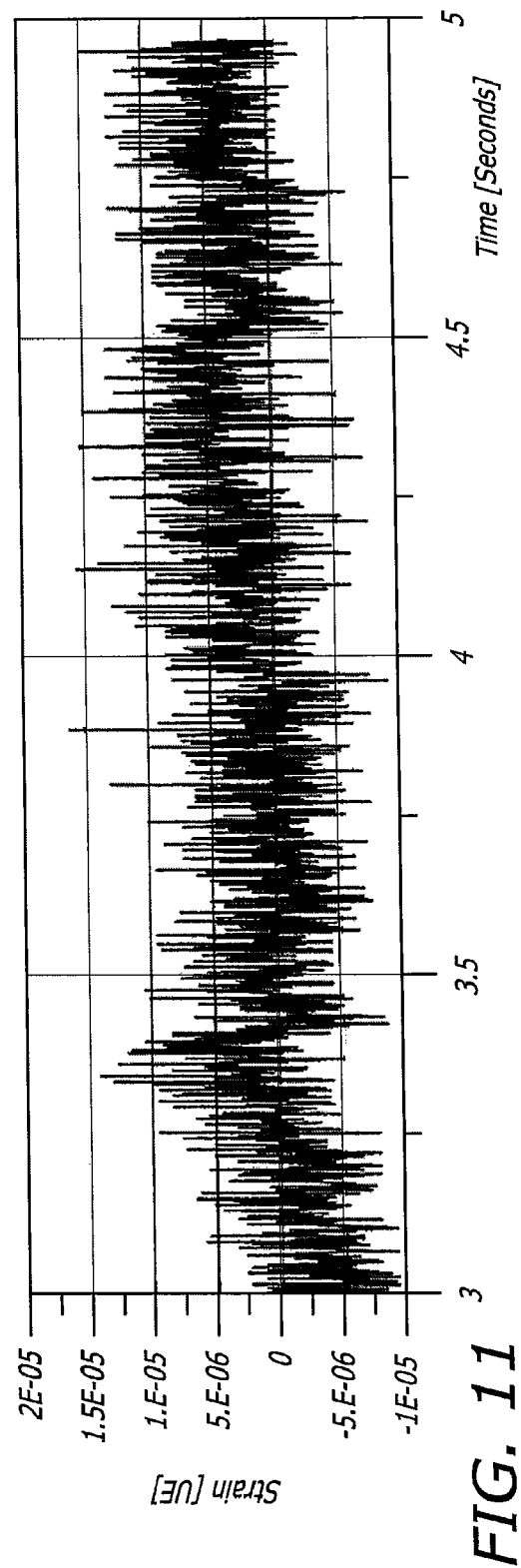
FIG. 11

METHODS AND TECHNIQUES TO MEASURE, MAP AND CORRELATE OCULAR MICRO-MOVEMENT AND OCULAR MICRO-TREMOR (OMT) SIGNALS WITH COGNITIVE PROCESSING CAPABILITIES IN ADD/ADHD INDIVIDUALS

CROSS-REFERENCES TO RELATED APPLICATIONS

This application claims priority from U.S. provisional Application No. 61/025,434, filed Feb. 1, 2008 incorporated by reference in its entirety.

BACKGROUND

The present invention is related to system and method for correlating optical micro-tremor signals with cognitive dysfunctions, and more particularly to a signal acquisition subsystem for obtaining at least one ocular micro-tremor signal, a signal processing subsystem for creating an ocular micro-tremor waveform and a correlation subsystem for comparing the ocular micro-tremor waveform to either a set of waveforms from populations of "normal" or fully functional cognitive individuals, or those of various classes of cognitively dysfunctional populations.

Advances in imaging technologies, along with a focus on the importance of cerebral processing in medicine and computer development during the last two decades, have provided the framework for many new approaches in both the theory and experimental data pertaining to the mind/brain interaction. During this period, newly formed departments of conscious awareness and cognitive science have appeared at university centers worldwide. Together with institutional research and development projects, scientists and philosophers from many disciplines have joined this quest: How indeed does the human mind perceive reality, form though and reason, and experience qualitative emotion through the elements of cognition? Much of the research has centered about developing an understanding of consciousness, and the role of awareness within that process.

The systems' architecture that would be required to meet these criteria could include brain matter proximal to the terminus of the neural switches, capable of storage of data through a quantifiable physical mechanism, and conductive within its own right. The latter requirement would be necessary to produce ongoing communication between neural segments, as the synaptic junctions would now only be switching networks. As will be pointed out below, this material could easily be postulated to be the brain's own support matter, the local glial cells. More importantly for the moment, the flow-down requirements on timing imposed by the second criteria on the mind/brain architecture requires expansion. The need for periods of off-time within the cycle of producing thought, recalling or storing memories, primarily related to sorting or finding facts probably fits comfortably within our own realms of experience. This type of general architecture could be constructed by postulating the existence of a master "process clock," against which all perceived cognitive events could be referenced. This may not be necessarily surprising, since other organs require timing periods for their operation such as the various muscle functions of the heart and peristalsis within the intestine.

The brain's intrinsic timing would have to allow for data input, retrieval, encoding (establishing a mechanism to allow it to be re-interpreted) and then de-coding. During these physical processes (some of which could conceivably be done in parallel within topologically non-coincident sites in the physical brain), a bifurcated periodicity must also exist where the brain is conscious-and-aware vs. conscious-but-unaware of underlying processes or choices. These two states are not dissimilar to the terms of consciousness or subconscious. The labeling is forcibly highlighted as always conscious, but aware part of the time, and unaware the rest of the time, to emphasize both the periodicity and exclusive need to have both states allowed with a continuous stream of data storage and recall. The unaware state is a definite requisite to accommodate the de-selection process discussed previously. Without it, one could be conceivably lost to the dementia of listening and/or seeing all the alternatives we have to pick from. Because of the fundamental requirement of having no dynamic memory manager, the conditions of awareness and unawareness cannot run simultaneously without the aforementioned cerebral process timing. Otherwise, it would take a cognizant function to know when to switch between states, and therefore, an a priori cognition of what conscious choice was to be made—a Herculean feat even for quantum mechanics.

A model proposed herein includes rapid blending of both states at the gamma band frequencies, typically centering about 40 Hz wherein the contents of consciousness are fused in much the same manner as the visual flicker fusion, audio fusion and tactile stimulus fusion experiments described earlier. To simplify terms, the process will be referred to as cerebral fusion. The contents of the cerebral cortex, as either experienced from the body's external sensors, or as perceived from memory and replayed through virtual sensor sites in the brain, integrate completely to form an ongoing vignette of scenes, thoughts and emotions. The systems description must further postulate that in no event can the mind sense the discreteness of the events. Complete continuity of consciousness at these cerebral process clock rates would prevent individuals from ever comprehending the detail between the windows of awareness. On the other hand, this same mechanistic process would allow for the appearance of simultaneousness between sounds and images occurring between temporally adjacent windows, even though we know that some audio stimuli arrive sooner to the cerebral cortex than do visual signals. Essentially, with the process of cerebral fusion, events can occur discretely, but near enough in time, and are captured during either an aware or unaware cycle (within about 20 to 50 msec). It is proposed that the mind will not discriminate between the separateness of the events, insofar as in this fusion process, the evolution of adjacent windows provides the illusion of continuity of thought. This concept is not dissimilar from the often-discussed binding problem.

Cerebral fusion may have three fundamental properties that allow for both blended information processing, and the observed sensory stimulation to perception delays. These properties are globalization, integration and persistence. Globalization refers to the ability of the cerebral workspace to respond to those areas across the cortex containing features of current thoughts. Since the fragments of pictures, words, associated smells, memories and sounds are not necessarily topologically co-located, the active centers contributing to an aware moment must be accessible to a centrex of processing (perhaps, the thalamus), much like a planetarium with a series of highlighted elements. This is conceptually not very different from a global workspace, with its attendant spotlight on the most current neural locations corresponding to the contents of a thought. At this juncture, no statement is made as to the interpretation of the discrete data items into recognizable images or sounds; what is implied within the globalization process is that all excited neurons are globally accessible and as such, are momentarily "highlighted." Integration refers to the process of assembling the quanta of thought elements described in the globalization process. As already discussed, together with the process of cerebral fusion, integration is a temporally driven capability of the brain wherein it is not possible for us to distinguish the non-simultaneity of successive events within one window of consciousness. The integration process guarantees that some fixed amount of time will be necessary post sensation before we are either partially depending on the elements currently undergoing globalization, or totally aware of what is occurring in the mind (or within the spotlight of the global workspace). At this juncture, integration assures that the recognition of already known or selected items can be made, but does not preclude the non-recognition effects of new items as well. Additionally, integration during unaware cycles allows for the de-selection of unwanted materials or intermediate results, as described earlier.

The establishment of a persistence component to cerebral fusion refers to a capability of individual neuronal sites to retain, with some finite lifetime, the contents of their stimuli that are undergoing integration during any one window. The observed nature of how human thought is continuous would require that sites be active for at least adjacent temporal windows (no less than 50 msec), but would not limit it to that minimum. In essence, this capability of the brain would enable the smoothing of memory and thought transitions from vignette to vignette. Persistence does not preclude sensory stimuli from appearing different to us if the actual input occurred simultaneously vs. separate in time (but within at least 50 msec). On the contrary, there are differences in tone and pitch of sound bites that are temporally separated by more than 15 msec. However, persistence will prevent the perception that each short stimulus (within 50 msec) appears discrete from its temporal neighbor. Persistence, as a feature of memory, would occur as a natural consequence of both ongoing sensory stimulus and the quenching or recovery times of neural nodes post stimulus. Whether or not neural nodes are electro-chemically induced or otherwise, there is an expected decay time post stimulus that is associated with the process and this would be consistent with the observed general properties of neural networks as well. Studies done with patients awakened from dream sleep stages show that these patients remember their dreams with varying clarity, indicating that neuronal persistence is indeed at work. In studies of various memory systems (direct recollection, short term recall, etc.) measured event related potentials have indicated windows to total awareness of times ranging from 350 msec to 1900 msec. Information perceived while unaware can remain in conscious memory for several hours.

The same concepts ring true in the areas of motor activation, when we walk without awareness of a stepping cadence, or drive a car without full awareness of the street details passing by. Some neuroscientists label this peripheral focus or absolute focus as part of a variable called "attention," but we would need to distinguish carefully between what is in our purview to "attend to" and what is not. The portion of consciousness that is forever in the unaware cycle cannot be the focus of conscious attention, because it will not yield to any level of concentration. Attention, as such, is a tool we use within the aware cycle to bring focus to one or one set of facts or events preferentially over another. By excluding others, or relegating them to subordinate roles, we are setting up the pieces that count in the complex thoughts that humans exhibit. Part of this facet of continuous consciousness contains what psychologists refer to as the subconscious. That term can be misleading though, because there is a suggestion that you can remember something or address something directly that is "just below the surface of awareness." This would only be true if one were to have contact with those intimate details and the mechanics of unaware thought—apparently not obtainable, since those mechanisms of the unaware processes are not subject to direct recall. As conscious awareness is but a fraction of the rapidly repeating and interleaved conscious cycles alternating between aware and unaware, and details of these unaware dynamics are not available within awareness, then the concept of a classical "subconscious" might have little meaning within this description. During the two phases of consciousness, aware and unaware (which is the sum total of all our conscious experience), we become conscious of everything around us that our sensory capabilities may have been stimulated with. We are only cognizant during the aware cycle, and thus have limited verbal reporting ability concerning the whole scene or everything we have sensed. It would then appear as if our brain "filled in missing details," but that would not be the case. Rather, we always "knew" what was in the scene, but were not "aware" of all of it in the part of the process we verbally report on, which is conscious awareness. Indeed, if we filled all the data in with our brain as a "construct," the resulting image in our mind would not necessarily comport as closely with actual photographs of the scene or the physical data; it would only be very rough approximations of them. Since we are indeed conscious of all the experiential content within this bimodal cycle, consciousness will appear continuous, despite only reporting on part of it during awareness.

Attention itself is an intended sensory focus on some portion of the data/emotion content of the current aware cycle. For an individual to "attend" to one specific fact, happening or emotion, or a set of the same occurring over many aware cycles to the exclusion of the rest of the scene would, in essence, be the equivalent of placing a blockade, or filter over the totality of the content being recalled during the unaware cycle, and only passing through the germane features matching those "attended" items. The analogy that best fits this picture is when we place a color filter in front of a camera used to take a photo in daylight, we selectively enhance the specific color items within the scene, and remove or diminish others. Attention, as a process, is potentially cued in as a sensory response that rapidly overwhelms the ever present "silent thought" data stream, and can subsequently be enriched by the ongoing cycles of the unaware mode. It is as if this bimodal system of consciousness must focus on something, and provide feedback during our waking moments. Attention deficit may actually be a misnomer, in that attention cues may not be missing or inadequate, but rather too plentiful, with not one of them dominate over the other.

The eyes are typically thought to be under voluntary control, with the responsible cortical areas located within the frontal cortex. However, eye motions occur in two fashions—smooth and slow controlled eye tracking in response to a moving object within the visual field, and in sudden jumps, known as saccades. The saccades themselves are bimodal, that is, there is a set of motions that have very short latencies (less than 100 msecs) known as express saccades, and a set of standard, sudden jumps (3 to 5 per second) that occur with high acceleration and deceleration rates that are for all practical purposes ballistic, even though deceleration is accomplished by simply stopping the input to the agonist (acceleration) muscles. The latter saccade movement (standard motion) is completed in 30 to 120 msecs, and then stays steady in "fixation." Fixations can last from 200 to 500 msecs. The express saccades, however, miss the visual target more often than the regular saccades, and have unpredictable gap durations. Whereas visual feedback cannot guide saccades, they appear to be guided by internal feedback of representations of a scene and a newly picked eye position. Most of the feedback originates in the superior colliculus. In short, the saccades appear as autonomic motions, with feedback from the mind to correctly re-align them to various targets. They are a collection of motions with trajectories and corrections resembling distributed data systems.

Oculomotor movements and saccades can be essentially both "windows" to conscious timing events, and hallmarks of the aware and unaware state transitions. To demonstrate this potential mathematically, one only need examine the literature for measured event times. These motor movements of the eyes can respond in a tonal fashion to lower frequency signals, and in a "twitching" fashion to high frequencies of up to 150 Hz. As a result of these capabilities, the eyes themselves display several different types of motions, categorically falling into two classes: major saccades and minor saccades.

Major saccades in humans are slow, visually observable motions of the eyes (generally commensurate with head movements) that are larger than 1.2 degrees, and driven by the 5 Hz or less tonal muscle motion. On the other hand, minor saccades can be subdivided into smaller motions, such as mini-saccades or flicks, and micro-saccades or tremors. These latter motions are not visible to the unaided eye, need special instrumentation to be observed, and are governed by the twitch muscles. The larger saccades typically occur over a 3 to 20 sec period, and are generally infrequent. The minor saccades are more regular, low amplitude movements that have been associated with object or group scanning. The most rapid and regular minor saccadic motion are the tremors, which are typically centered at about 90 Hz, but have been measured in ranges between 30 Hz and 100 Hz. Their duration lasts 10 to 20 msecs. The mini-saccades occur at a rate of 3 to 5 per second for a typical duration of 25 to 30 msecs. Both these types of motion will occur during "voluntary" fixation, that is, despite our controlling where our focus (or attention) is centered. Even though the tremors are smaller amplitude changes in eye position, they are enough of a displacement that they should, theoretically, blur vision, but they don't. The mini-saccades have larger amplitudes, occur at theta frequency rates, and have been theorized to be larger corrective displacements to overcome the drifts produced by tremors. Insofar as mini-saccades occur during fixations, and have been correlated to visual attention, their transitions may represent shifts of attention or refocus. Their amplitude and frequency should also contribute to a distortion of experienced visual images, but again, they do not in conscious awareness. The saccades themselves also respond to feedback, that is, there are adjustments made movement by movement to new items presented within the field of view. However, the actual time of movement, taken from the appearance of a new item (target), is smaller than the overall fixation period.

Certain motions of the eye would then offer an opportunity to present diagnostic information about the processing of consciousness content, or better yet, the dysfunctional outcomes due to impaired timing from brainstem regions as reflected in those eye motions. Current studies show that eye micro-tremors can be an indication of the general state of consciousness, including the depth of anesthesia, as the number of tremors become fewer as the individual approaches unconsciousness. Along with the frequency of eye tremors, the latency of saccadic motion, range of motion, and fixation stability are among other changes that can prove to be diagnostic. Saccadic anomalies have been used as part of diagnostic testing of patients with Multiple Sclerosis and Parkinsons Disease. Likewise, other neurological disturbances such as Huntington's Disease and Attention Deficit Hyperactive Disorder (ADHD) have had ongoing research showing correlation of established diagnosis with changes in saccadic eye motion. If, as the new theory developed by the inventor herein suggests, the micro-eye movements are reflections of the autonomic timing for the natural interleaving of the conscious aware and unaware states, then changes in that timing and signature components could potentially be demonstrated as altered or impaired neurological functions. Incomplete aware timing could possibly disturb neurological signs of awareness and attention, and incomplete unaware timing could affect motor neuron transmissions, among other processes.

It is known that disorders such as Parkinsons Disease, Huntington's Disease and Tourette's syndrome share a common region of the brain that is associated with some of the motor difficulties, especially in the basal ganglia. Since the origination of the signals causing involuntary eye motion, and the aware/unaware windows of consciousness are tied through or within similar areas, it can be argued that the direct observation of eye movement abnormalities due to these disorders and the corresponding motor symptom appearances are related. However, since the origination points are within the basal ganglia structures and the autonomic systems, these influences are not occurring through consciousness pathways, just through the timing areas of the brain responsible for the bimodal portions of consciousness, aware and unaware. Typically, the basal ganglia can be responsible for true weakness, as noted in some Disease states. However, such disorders can display a full range of abnormality, not limited to just "weakness" of motor responses. These include affects of the ease and speed of motion. Additionally, both Parkinsons Disease and Multiple Sclerosis patients concomitantly display cognitive changes. Therefore, the observations for these two physical disorders appear to be more complex than just the currently recognized neuro-physical impairments noted in the literature, and could infer correlations beyond the coincidence of similar brain structure involvement. Surely the psychological issues within schizophrenia are more "cognition" issues than motor issues as are those of ADHD. Measurements made on schizophrenic patients have shown demonstrable changes in saccadic reactions concomitant with impaired information processing. Studies on patients diagnosed with ADHD have shown impairment of fixation and saccadic movements as compared with normal patients. Likewise, administering Ritalin (methylphenidate) appears to strengthen saccadic control and weakens strong fixations. Even though the saccadic and tremor eye movements are windows to the autonomic conscious timing events, and not a basic "driver" of the system, this new theory infers that the eye motions are also demarcation movements of the changes of "attention" within consciousness. Insofar as the tremors can be observed as part of the overall eye motion, theoretically, these movements could be studied as to their changes (if any) produced while forcing shifts in attention, or the reverse. This represents a relatively new area for research: to examine if consciousness mechanisms can be used to alter consciousness dynamics.

Since eye motion, attention and ultimately feedback are the major control items within the cyclical consciousness expounded in this model, they are also important to the modification of consciousness. Even though cyclical timing is autonomic, the data elaborated in this paper show that the cycle itself can be disrupted: it occurs in biofeedback, Eye Movement Desensitization and Reprocessing (EMDR), trance and other therapies. The recognition that eye motion represents a physical portal to timing is novel, and can allow for extended research in changes produced by drugs as well as changes accompanying various cognitive aberrations. It is interesting to note that those having ordinary skill in the art have aptly labeled the conscious process as one that contains the feeling of the body's emotional states, and in reality, we indeed feel all that occurs within us, because we are continuously experiencing it while it is integrated with other sensory stimuli. However, we only report on and talk about what makes it into our "awareness." All of it will ultimately shape how we think, even those portions resident only in our unaware and unattended consciousness because of the regular cycling of the aware and unaware states.

Accordingly there is a need for, and what was heretofore unavailable, a system and method for correlating ocular micro-movement and ocular micro-tremor signals with cognitive dysfunctions. The present invention solves these and other needs.

SUMMARY OF THE INVENTION

The present invention is directed to a system and method for correlating ocular micro-motion and micro-tremor signals with cognitive dysfunctions. The system includes recording a tremor signal, and a signal processing subsystem for creating a waveform from at least one acquired ocular micro-tremor signal. The ocular micro-tremor waveform from an unknown or psychologically diagnosed individual is compared to both a waveform algorithm or emulation from a set of normal cognitives, or those derived from cognitive dysfunctional groups to determine the actual true cognitive dysfunction of that patient. The signal acquisition subsystem may be configured using any physical sensor capable of measuring these small motions, such as an optical sensor, a piezoelectric sensor, strain gauges or accelerometer sensors, a CW (continuous wave) light wave emitter, a pulsed light wave emitter, a sonic wave emitter, or an airflow system, to name a few. The patient's or individual's cognitive waveform may then be compared to that of an ADHD waveform, an Attention Deficit Disorder (ADD) waveform, another unknown patient's waveform, an autistic waveform, or any cognitive dysfunctional waveform desired, or those of a set of cognitive normal groups. The invention is intended to be an apparatus to physically display and diagnose cognitive processing normal populations and cognitive processing of abnormal populations, and perform diagnostic comparisons between those sets and that generated by an unknown patient. It is also envisioned that the same apparatus can compare the signals derived from patients both before, during and after therapeutic treatments are administered to evaluate the effects of those therapies.

The present invention is derived from a logical systems flow-down of a set of consciousness requirements, which together with biological quantification of human brain anatomy sets limits on the neurological network in the cerebrum in order to produce the mind. It employs data (where available) to validate inferences, or when data do not exist, proposes methods for acquiring valid evidence. Many of these systems requirements will be imposed after some fundamental assumptions are made. These assumptions are not new to theories on consciousness. However, their application as fundamentals may actually represent a new approach. Concurrent with these fundamentals, explicit periods of awareness while conscious are employed. Justification for their use is found in a theoretical process described as cerebral fusion. Additionally, storage of memory elements is postulated within local glia sites, proximal to synaptic nodes, and conductive transport through the astrocytes responsible for recall of data. The model permits variations in neural-glial interface physics and allows forecasts of mind-brain dysfunctions to be inferred. One key result from the model is hypothesized and expanded upon, and may have impact in certain types of dementia, such as Alzheimer's Diseases. (Lonky, M. (2003). Human consciousness: A systems approach to the mind-brain interaction. *The Journal of Mind and Behavior*, 24, 91-118; the content of which is hereby incorporated herein by reference.

The continuity of consciousness is a reality, provided by the blending of the combination of both conscious aware states with conscious, but unaware ones, and where the frequencies governing the interleaving of the two states prevent us from ever directly deciphering the nature of their discrete properties. As a consequence, we cannot experience any discontinuity within the global phases of consciousness itself. The impact of this continuous cycling has major implications towards the purpose and mechanics of the aware cycle within the conscious process, as well as the role of attention. A model is presented wherein these cycles are mirrored in ocular motion, and both are related to autonomic mechanisms. Concepts are presented that argue for the aware state function to be largely centered on the management of attention, while providing feedback to the unaware cycle. The empirical concept developed is then tested against both current experimental data and several longstanding consciousness processing conundrums, with favorable results. (Lonky, M. (2006)). Human consciousness: A revised view of awareness and attention. *The Journal of Mind and Behavior*, 27, 17-42; the content of which is hereby incorporated herein by reference.

BRIEF DESCRIPTION OF THE DRAWINGS

FIG. 11 depicts a graph illustrating strain over time for patient Andrew.

DETAILED DESCRIPTION OF THE PREFERRED EMBODIMENTS

Figure 1:
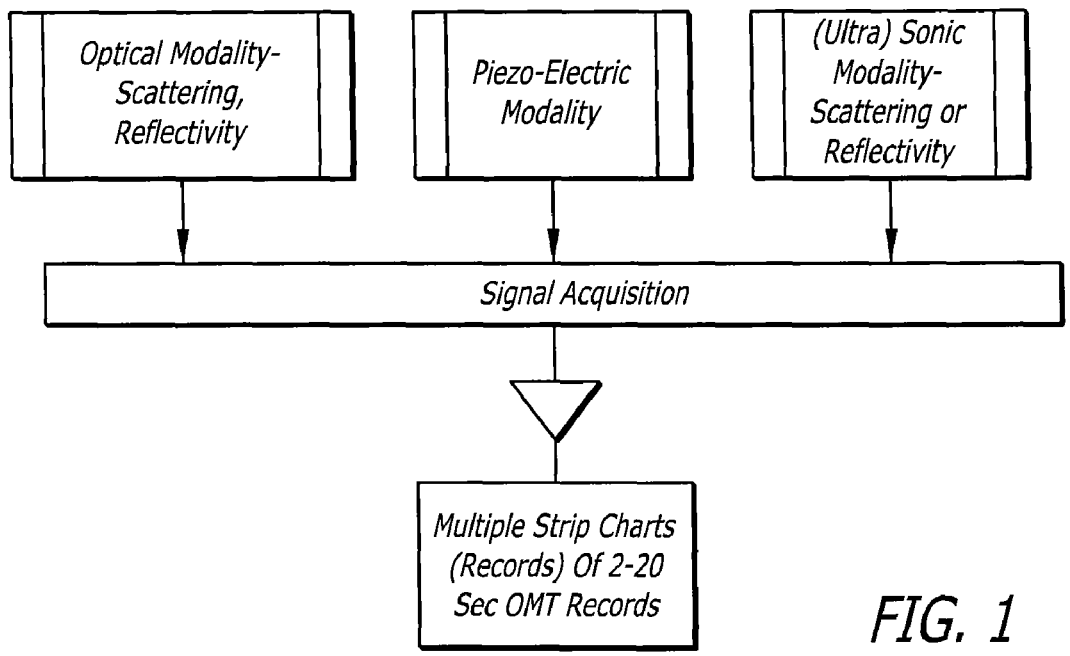
FIG. 1 is a schematic representation of an ocular micro-tremor signal collection subsystem of the present invention.

Ocular micro-tremor, or OMT, has been classically described as a very small motion of the eye, which is constant, typically at an average frequency of about 80 Hz, and varying in amplitude from 150 nm to 2500 nm. It occurs in all humans, and has been related to the activity produced within the brainstem region (lower reptilian brain which sits on the top of the spinal column). It was first reported on by Adler et al. in 1934 (Adler, F. H. M., Fleigelman, Maurice, A B, (1034), "Influence of Fixation on the Visual Acuity," *Archives of Ophthalmology*, 12: 475-483.) Since it only ceases at death, the measurement of the tremor has been a useful tool in evaluating people under anesthesia, and in a coma (see for Example, references 1-3). Additionally, having its origin within the brainstem, abnormalities in ocular micro-tremor patterns have been noted in several neuromuscular disorders such as Parkinsons Disease and Multiple Sclerosis (see, e.g., Bolger, C., et al., "Ocular micro-tremor (OMT): a new neurophysiological approach to Multiple Sclerosis," *Journal of Neurological Neurosurgery Psychiatry*, 68(5): 639-42, 2000; and Bolger, C., et al., "Ocular micro-tremor in patients with idiopathic Parkinsons Disease," *Journal of Neurological Neurosurgery Psychiatry*, 66:528-31, 1999). Additionally, some work has been done to show that an average frequency change is concomitant with age (see, e.g., Bolger, C., et al., "Effect of Age on Ocular Micro-tremor Activity," *Journal of Gerontology, Series A*, 56:M386-M390, 2001).

This represents the total area of published work concerning OMT. While there are a number of other papers exploring the ability to repeat this data on other groups of similar patients, the subject matter covered in those studies has always remained "the study of OMT frequencies and their relationship to brainstem activity in the semi-conscious patient and in the neuro-physically impaired patient."

A number of different apparatus methods have been employed in collecting this data, including using piezo-electric strain gauges directly in contact with an anesthetized eye, accelerometers on closed eyelids, and concepts involving laser interferometry as a non-eye-contacting device. All the reported apparatus developed by the several authors who have contributed to the literature have essentially provided the same type of waveforms for OMT, and demonstrate consistent data regarding correlation to brain stem activity in assessing patients receiving anesthesia or in comas.

Martin Lonky, in 2003 (*Journal of Mind and Behavior*, 24:1, pp. 91-117) published a theoretical concept concerning a physical mechanism that could explain experimental data published on several aspects of human consciousness and cognition. The models developed employed a two phase conscious state comprised of contiguous aware and unaware periods. A second paper published in 2006 (*Journal of Mind and Behavior*, 27:1, pp. 17-42) showed that this model could actually account for several measured consciousness processing conundrums, such as binocular rivalry and Shapiro's EMDR work (eye motion and desensitization reprocessing).

The present invention is new and unique and is based on making a new connection between the bimodal format of the consciousness periods defined in the aforementioned papers, and the origin of the signal that could control that timing. The signal most probably originates as part if the autonomic nervous system in a region proximal to the superior colliculus of the brain, close to the region responsible for the neurologically driven OMT motion of the eyes. It is this concept, along with the scientific hypothesis that the OMT motion can provide a window to the cognitive processing of a human being, that forms the basis of the invention.

The present invention demonstrates experimentally that OMT changes are responsive to changes and degradations in cognitive processing. These phenomena are regulated and performed in regions in the mid-brain and above, including the cerebral cortex.

The traces of the OMT from the eyes have been attributed to a correlate to the dual consciousness states (aware and unaware) that, it is postulated, is part of human cognition. Normal functioning humans (people with no measured cognitive defects or dysfunctions) ought to fit into a series of waveforms that have similar attributes (central frequencies, frequency content, amplitudes, waveform shapes, rise times, fall times, etc.) and be describable (cognitive capabilities) in terms of those and other features. In fact, since there should be no expectation that any two people (within a normal cognitive range) should have "exactly the same features" within the way they process and transact information, normal functioning human subjects should fall into a "band" of allowable characteristics with their specific signature pattern.

Likewise, cognitively challenged or cognitively dysfunctional subjects should fall into a "bands" of descriptive OMT signature components. For example all subjects correctly diagnosed with ADD or ADHD should fall into a group of similar descriptive schizophrenia, etc. Again, no two patients with the "same" diagnosis will be exactly the same, but rather exhibit a class of similarities between themselves that is different from those of a cognitively normal population. In some sense, these parametric characteristics of a patient's physical OMT signature pattern is a form of differential diagnosis of cognitive capabilities (or cognitive disabilities, as the case may be). Again the technique can be applied (as a "before" and "after" screen) to evaluate the benefits or shortfalls of therapies used to treat these dysfunctions. For example, an ADHD patient taking Ritalin (methylphenidate) may show improvements in their signature parametric values, perhaps approaching those of normal cognitive processing individuals. Likewise, the value of behavioral or cognitive therapy or biofeedback may also be evaluated in terms of changing a patient's OMT signature pattern toward a more beneficial class of parameters. These are "new" methodologies for processing, categorizing and comparing components of OMT signatures and wave forms for correlation, diagnosing, and evaluating therapies for cognitive disorders and dysfunctions.

When viewed this new way, even the older published work on Parkinsons Disease and Multiple Sclerosis may now be more related to the cognitive disorders concomitant with those neuro-muscular Diseases than the neuro-muscular dysfunction itself. This new technological method for evaluating the OMT motion signals of the eyes probably explains why there are a band of values observed within the reported (literature) studies on these Diseases, rather than a single value associated with each disorder. It is because the OMT motion itself is truly tied to the cognitive losses and decay of that particular patient, not the fact that the subject has (for example) Parkinsons Disease, i.e., each patient would be expected to have a different level of cognitive dysfunction (or conversely, remaining cognitive capability).

I. Signal Acquisition

As shown in FIG. 1, the system and method of the present invention provides for selecting a methodology for acquiring (as an example) ocular micro-tremor (OMT) measurements from an individual patient. The system may be configured to use either the existing forms of piezoelectric sensor apparatus units currently available, or newer formats using CW or pulsed light wave, sonic wave emitters, or steady-state or intermittent air flow apparatus, stain gauge sensors, miniature accelerometers, etc., all with low-noise, calibrated sensors to discriminate low amplitude (approx. 200 micron to 5,000 micron motions) and low frequency (approximately 90 Hz)

Figure 4:
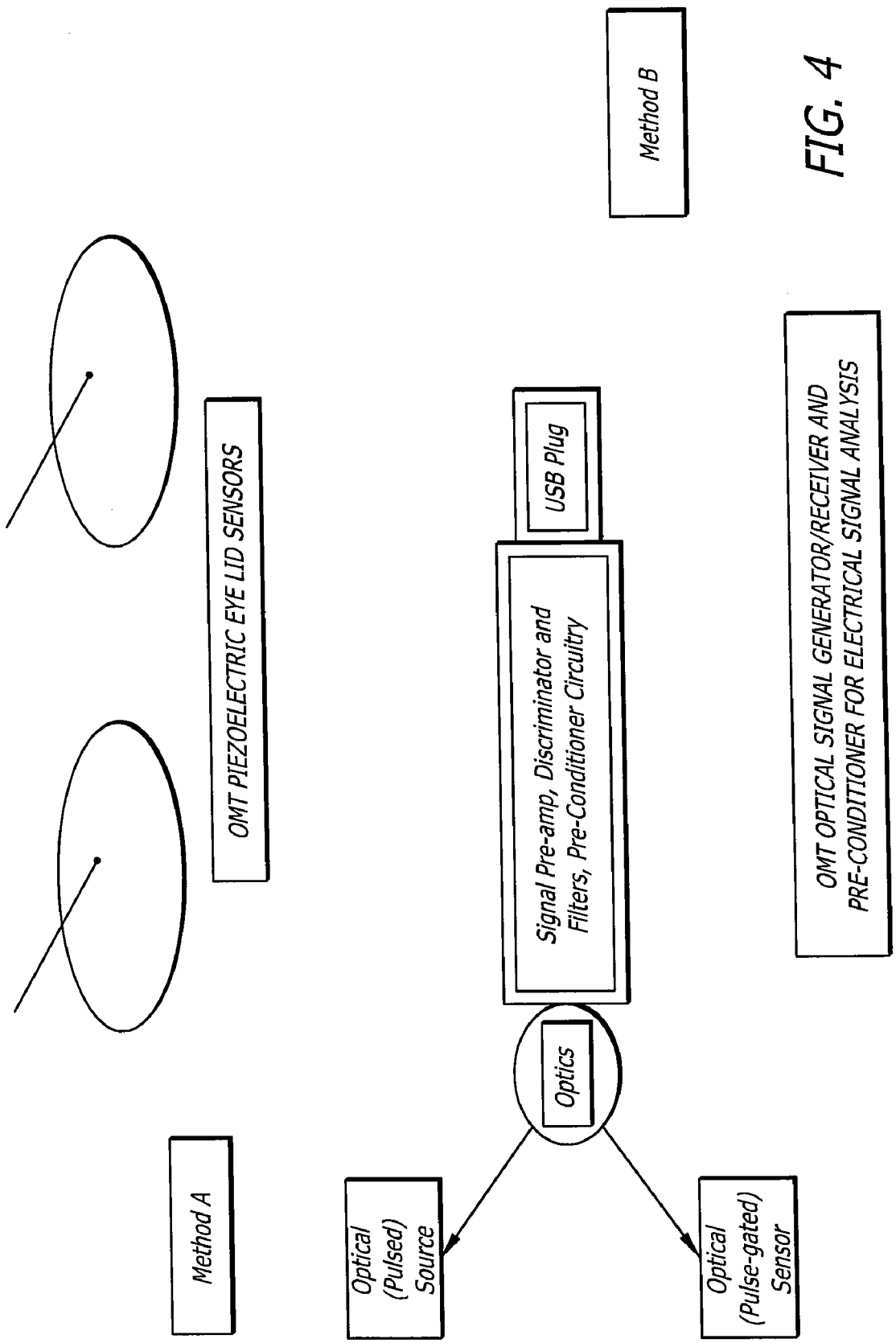
FIG. 4 depicts one embodiment of a sensor system of the present invention.

OMT ocular motions (see, for example, FIG. 4). Suitable systems may be found in U.S. Pat. No. 7,011,410, and U.S. Publication No. 2006/0082727 both of which are incorporated by reference herein. These may also include methodologies that could be derived from more sensitive versions of eye tracking hardware and modules that presently are used to measure ocular micro-saccades, drift and flicker. The system may be configured to record two to twenty second waveform sequences from the patient, several times during the acquisition.

II. Define Waveform "Signature"

Figure 2A:
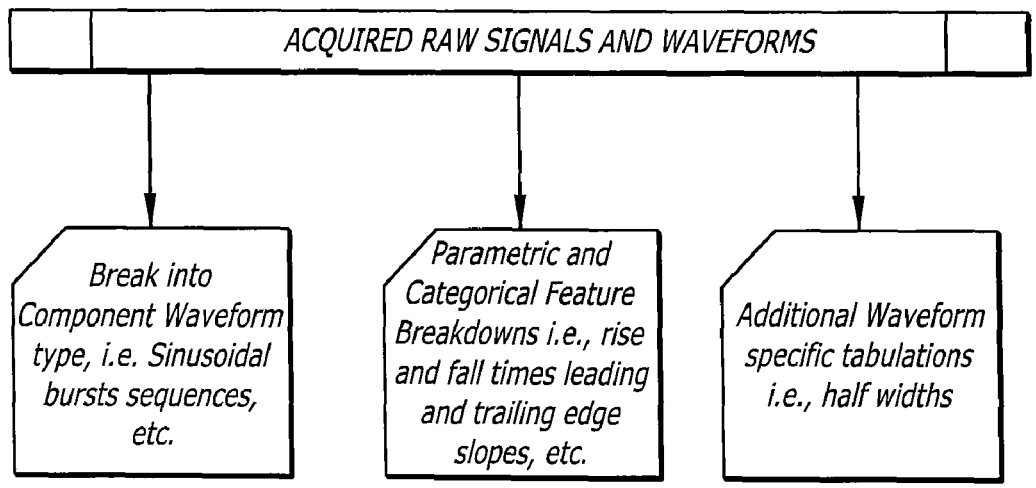
FIG. 2A is a schematic representation of a signature assembling subsystem of the present invention.

Referring now to FIG. 2A, OMT waveforms contain several repeatable elements or sequences, including sinusoidal components, burst components, spindles, and spacing or voids. The signature measured is an analytical description of the continuous waveform's composite information. The present invention incorporates an algorithmic system capability to measure and define leading edge rise time slopes, as well as trailing edge fall times and slopes of repetitive sinusoidal components of the OMT waveform. Midpoint and half-widths of repetitive sinusoidal components of the OMT waveforms may be measured and defined as well. Further, the system may be configured to measure and collate separations between peak intervals, measure frequency of burst packages and waveform frequency of bursts and sinusoidal components.

The system and method of the present invention may be further configured to note and annotate spindles that may accompany waveforms, and incorporate their presence in the signature description. The average and mean frequency of the waveform composite, including the various elements that comprise the OMT signature, are characterized and measured, i.e., the sinusoidal packet and the burst elements. In addition, the system may be configured to note and measure the time intervals between any voids between OMT packets, and configure the waveform signature with this spacing, if any. The system may also be configured to note the mean amplitudes and the extrema of both the sinusoidal portions and the collective bursts.

The system is further configured to categorize the signature both graphically and parametrically and to perform transforms on signature parametric characteristics, including, but not limited to Fourier Transforms. The system would either add a new signature to the sets of "known cognitive classes databases," or use it as a comparative against other known sets, to define the most likely classification of cognitive processing that the new signatures represent or belong within. In the event the signature is compared to itself from an earlier stage, or pre-therapy or medication, the system notes the changes brought about by the intervention (if any) by movement towards a "normal" or otherwise beneficial cognitive improvement.

Figure 2B:
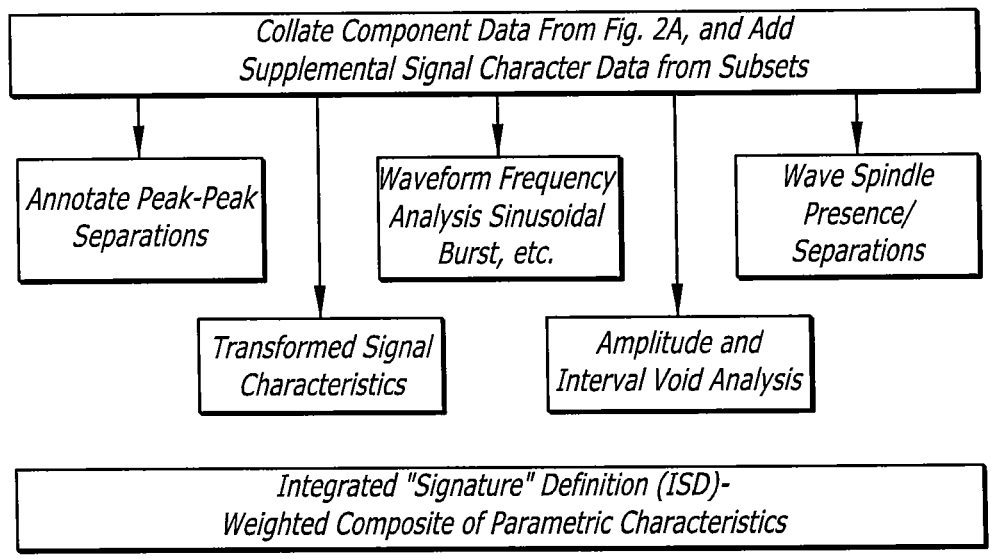
FIG. 2B is a schematic representation of an ocular micro-tremor signature definition subsystem of the present invention.

III. Signature Characteristics to Define Families of Cognitive Processing Varients As shown in FIG. 2B, the system and method of the present invention captures and defines the characteristic signature and properties of various states of cognitive dysfunctions, as well as those belonging to a set of "cognitive normals," in both a documented and algorithmic library for analytical comparisons. These states include, but are not limited to, ADD, ADHD, Autism, Bipolar thinking, Obssessive Compulsive Disorder (OCD) thinking, Schizophrenia, and Alzheimers Disease.

Figure 3:
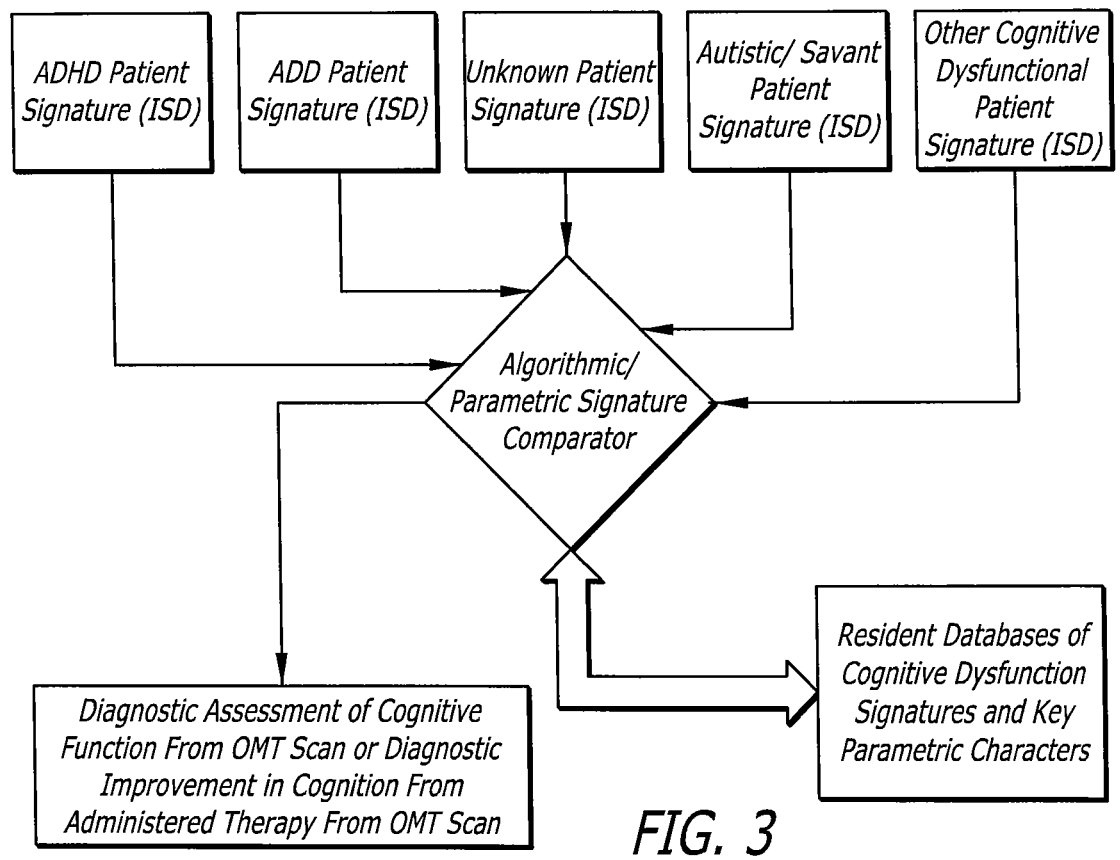
FIG. 3 is a schematic representation of a diagnostic assessment subsystem of the present invention.

IV. Use of these Libraries of Signatures and Captured OMT Measurements to Corroborate Psychological Diagnoses or Generate Physical Diagnoses of Cognitive Processing Classifications As shown in FIG. 3, the system and method of the present invention collates signature parameters within populations of "cognitive normals," "cognitive ADD," "cognitive ADHD," "cognitive Autistic," etc. Within each cognitive set, the system assembles the parametric elements of the signature into a weighted priority deterministic equation, to be used for matching unknown patients, or patients undergoing therapy or remedial treatment. The system of the present invention further establishes a "statistical" compare function across all the weighted sets for any new "unknown patient condition" or new patients in general. In addition, the system may be configured to update patterns regularly with new standardized data sets from established clinical trials.

FLOWCHART FOR: Methods and Techniques to Measure, Map and Correlate Ocular Micro-tremor (OMT) Signals with Cognitive Processing Capabilities I. Signal Acquisition
  a. Select methodology for acquiring OMT measurements from individual patient.
  b. Use either the existing forms of piezoelectric sensor apparatus units (FIG. 4) already in literature (patented, i.e., EYETECH), or newer formats using CW or pulsed light wave or sonic wave emitters, with low-noise, calibrated sensors (FIG. 4) to discriminate low amplitude (approx. 200 micron to 5,000 micron motions) and low frequency (approximately 80-90 HZ) OMT ocular motions.
  c. Record 2 to 20 sec waveform sequences from the patient, several times during the acquisition.

II. Define Waveform "Signature"
  a. OMT waveforms contain several repeatable elements or sequences, including sinusoidal components, burst components, spindles, and spacing or voids. The signature measured is an analytical description of the continuous composite waveform.
  b. Measure and define leading edge rise time slopes, as well as trailing edge fall times and slopes of repetitive sinusoidal components of the OMT waveform.
  c. Measure and define midpoint and half-widths of repetitive sinusoidal components of the OMT waveforms.
  d. Measure and collate separations between peak intervals.
  e. Measure frequency of burst packages and waveform frequency of bursts and sinusoidal components.
  f. Note and annotate spindles that may accompany waveforms, and incorporate their presence in the signature description.
  g. Characterize and measure the average and mean frequency of the waveform composite, including the various elements that comprise the OMT signature, i.e., the sinusoidal packet and the burst elements.
  h. Note and measure the time intervals between any voids between OMT packets, and configure the waveform signature with this spacing, if any.
  i. Note the mean amplitudes and the extremas of both the sinusoidal portions and the collective bursts.
  j. Categorize the signature both graphically and parametrically.
  k. Perform transforms on signature parametric characteristics, including, but not limited to Fourier Transforms.
  l. Either add signature to the set of "known cognitive classes database" or use as a comparative against known sets for defining the most likely classification of cognitive processing capabilities in which the new signature belongs.

m. In the event the signature is compared to itself or from an earlier stage, or pre-therapy or medication, note the changes brought about by the intervention (if any) by movement towards a "normal" or otherwise beneficial cognitive improvement.

III. Use of Signature Characteristics to Define Families of Cognitive Processing Variants a. Capture and define the characteristic signature and properties of various states of cognitive dysfunctions, as well as those of cognitive normals in both a documented and algorithmic library for analytical comparisons.

b. These states include, but are not limited to, ADD, ADHD, Autism, Bipolar thinking, OCD thinking, Schizophrenia, and Alzheimers Disease.

IV. Use of these Libraries of Signatures and Captured OMT Measurements to Corroborate Psychological Diagnoses or Generate Physical Diagnoses of Cognitive Processing Classifications a. Collate signature parameters within populations of "cognitive normals," "cognitive ADD," "cognitive ADHD," "cognitive Autistic," etc.

b. Within each cognitive set, assemble the parametric elements of the signature into a weighted priority deterministic equation, to be used for matching unknown patients, or patients undergoing therapy or remedial treatment.

c. Establish a "statistical" compare function across all the weighted sets for any new "unknown patient condition" or new patients in general.

d. Update patterns regularly with new standardized data sets from established clinical trials.

Experimental Data

Figure 5:
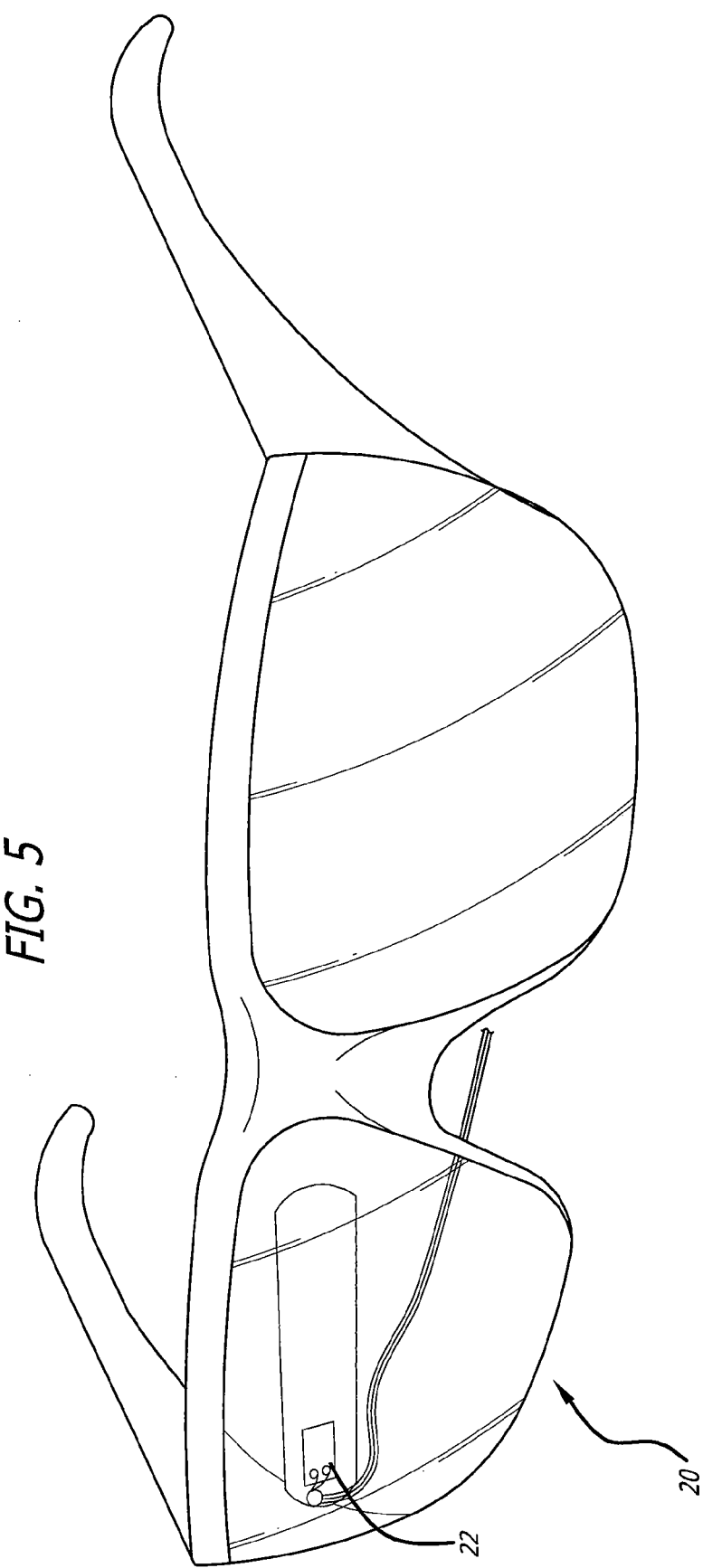
FIG. 5 is a partial plan view of a pair of safety glasses with a sensor for measuring ocular micro-tremors.
Figure 6:
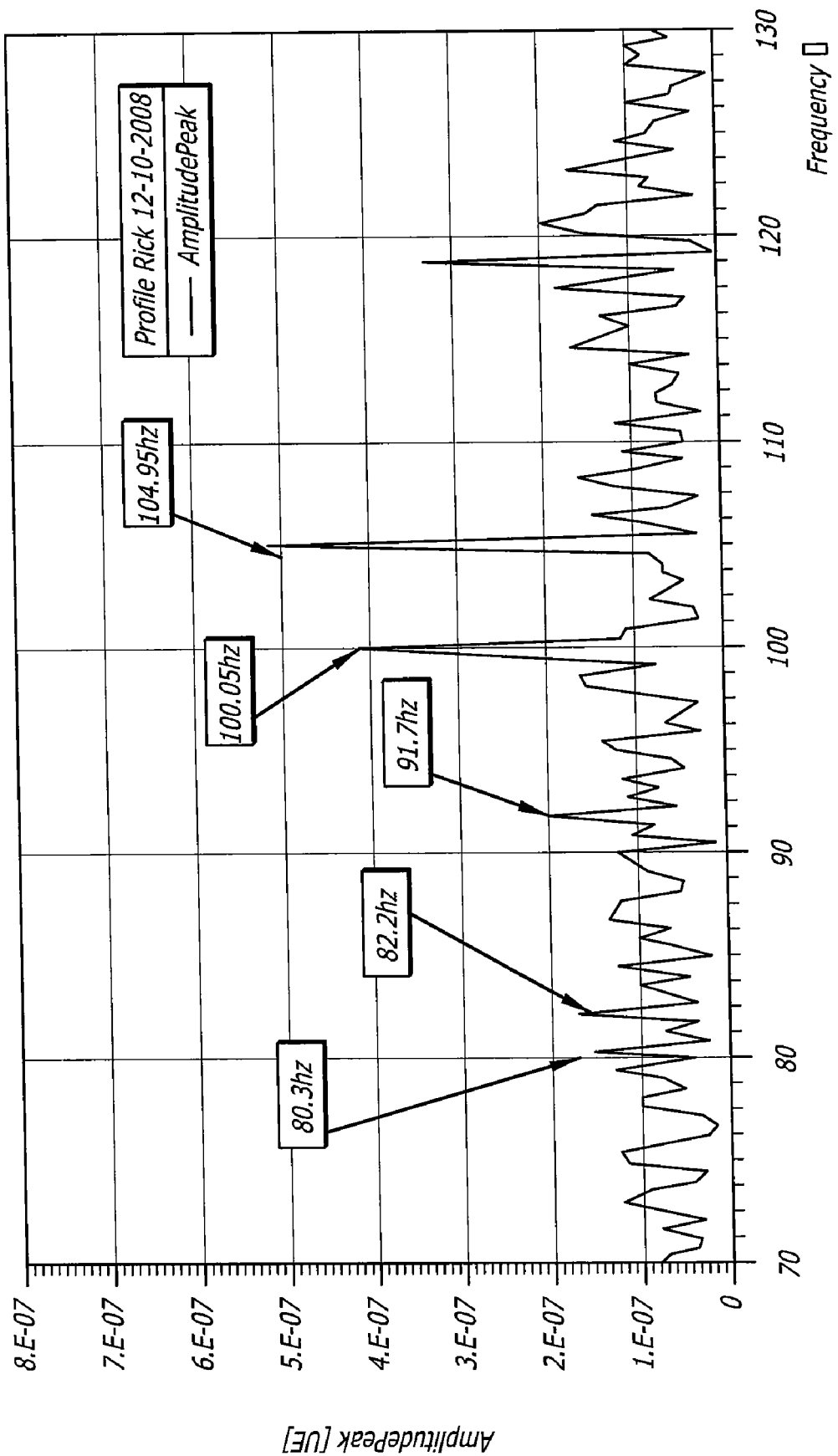
FIG. 6 depicts a graph illustrating the amplitude peaks over time for patient Rick.
Figure 7:
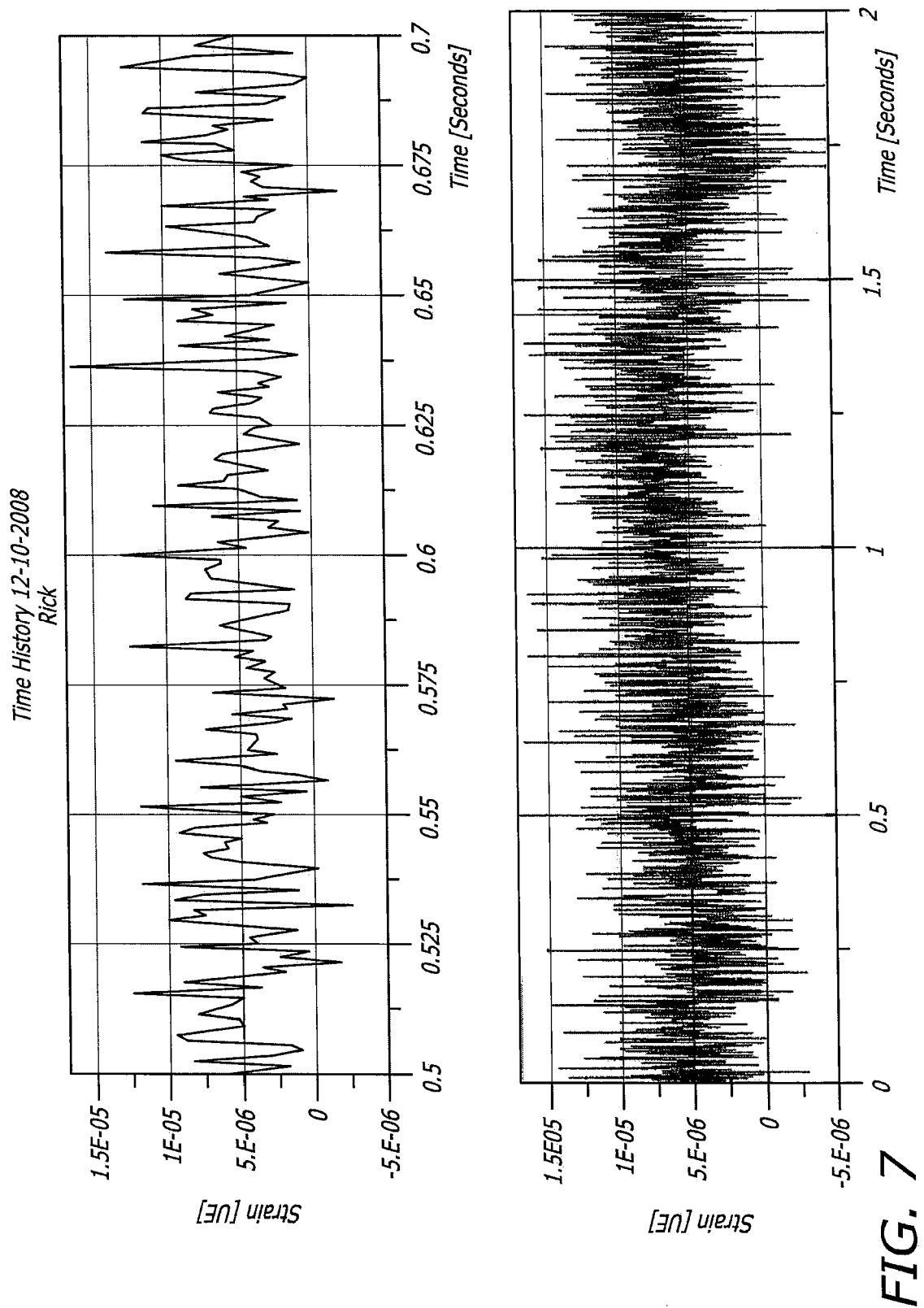
FIG. 7 depicts a graph illustrating the time history of the strain for patient Rick.
Figure 8:
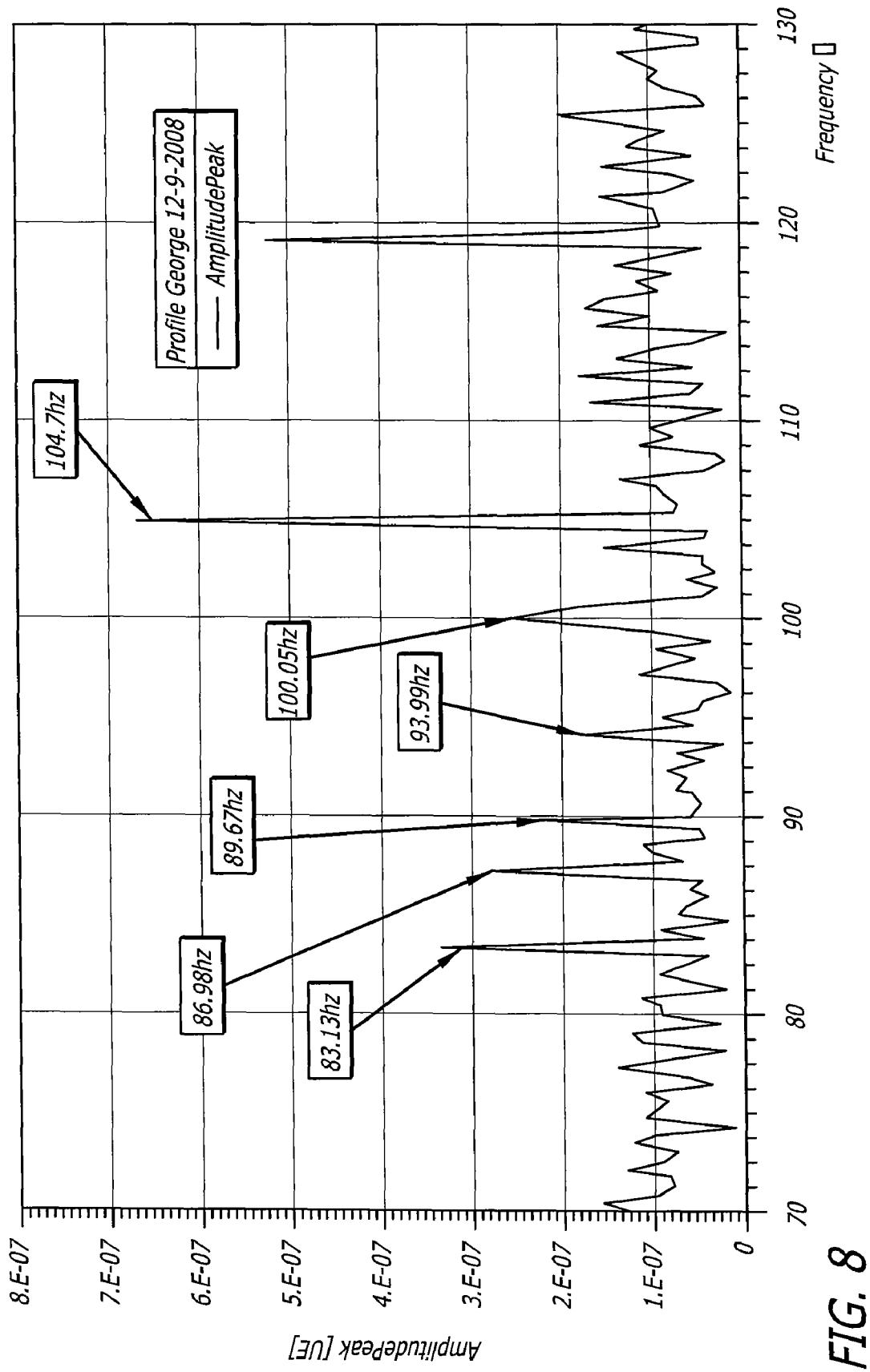
FIG. 8 depicts a graph illustrating the amplitude peaks over time for patient George.
Figure 9:
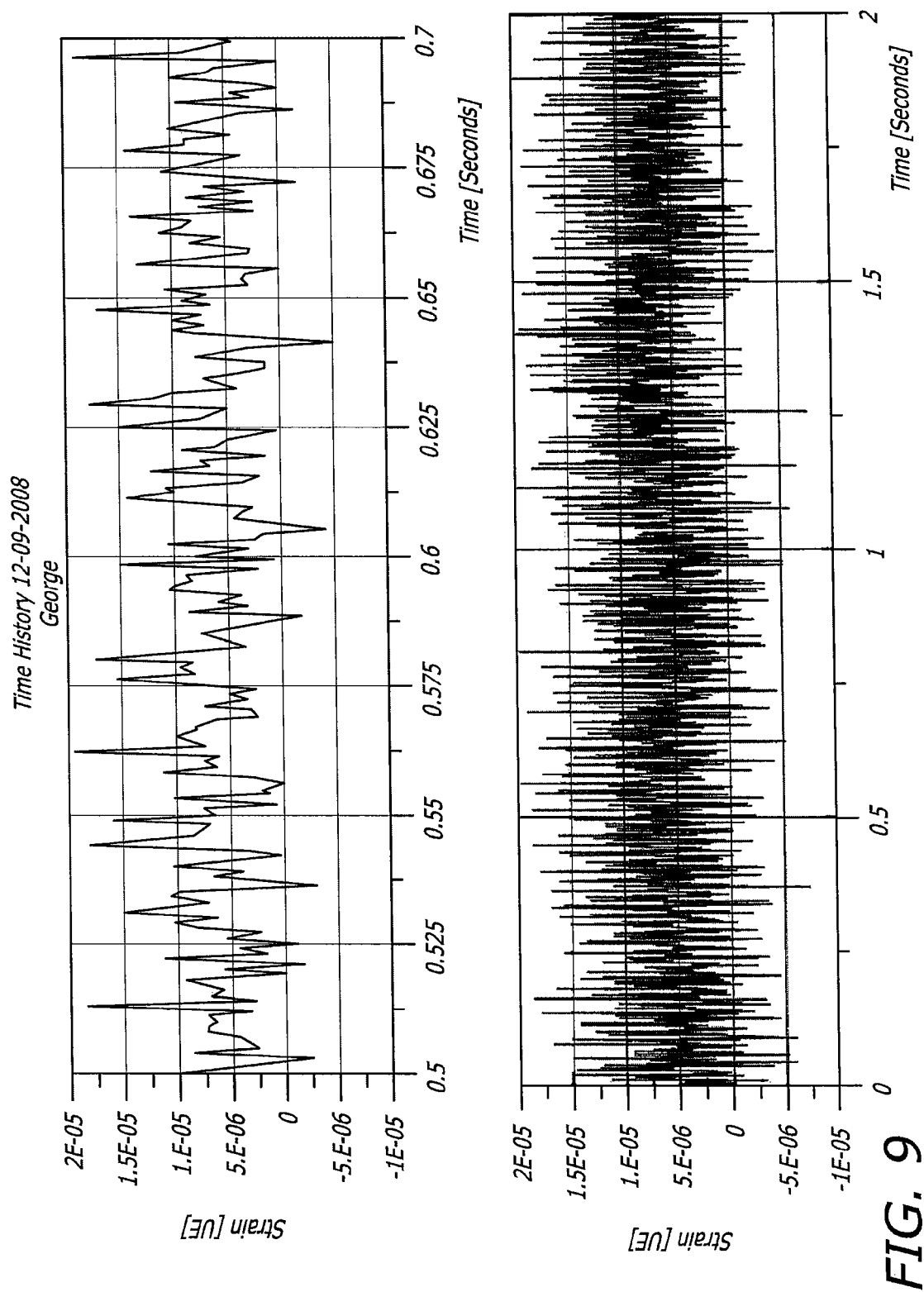
FIG. 9 depicts a graph illustrating the time history of the strain for patient George.
Figure 10:
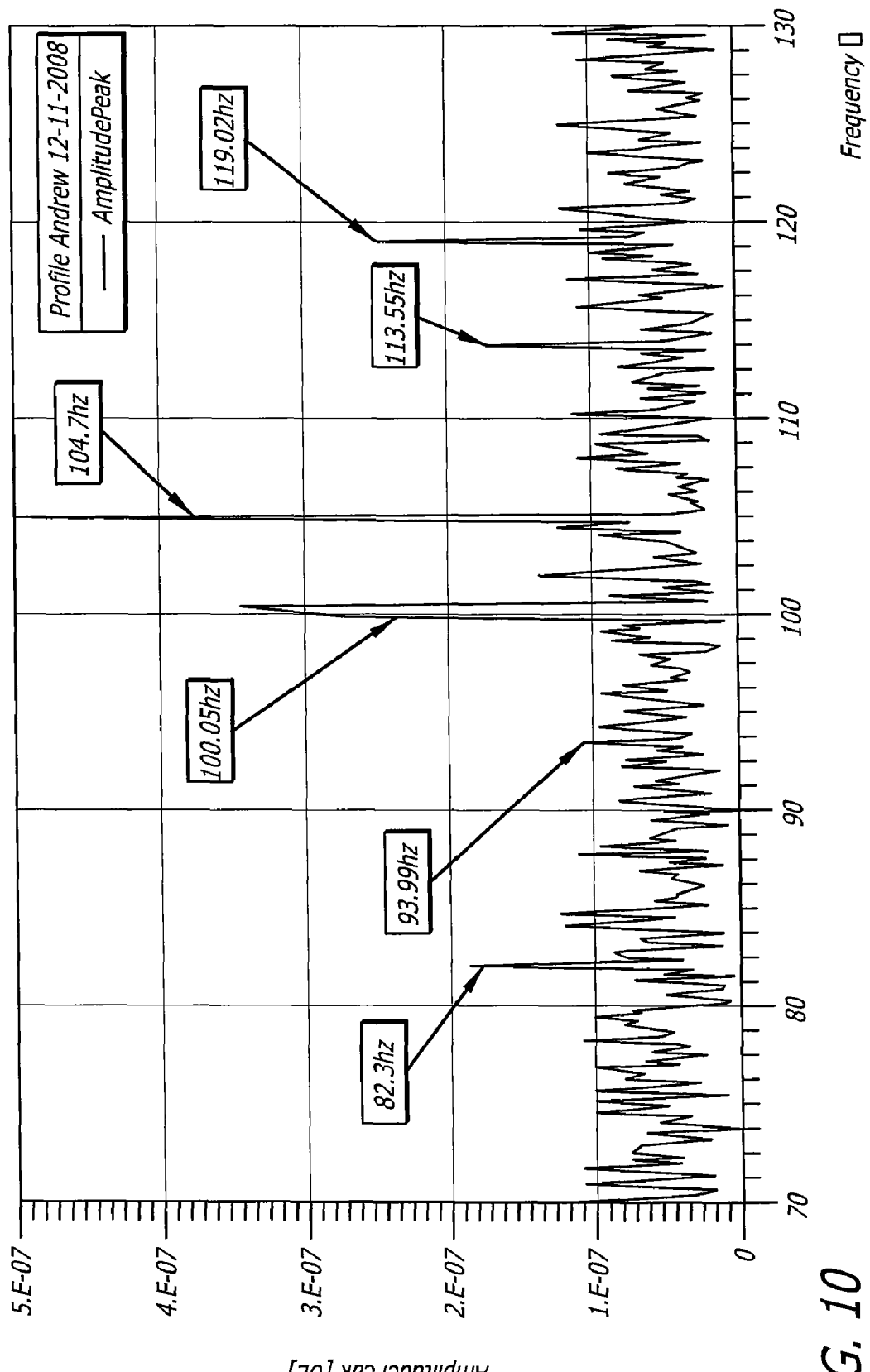
FIG. 10 depicts a graph illustrating the amplitude peaks over time for patient Andrew.
Figure 12:
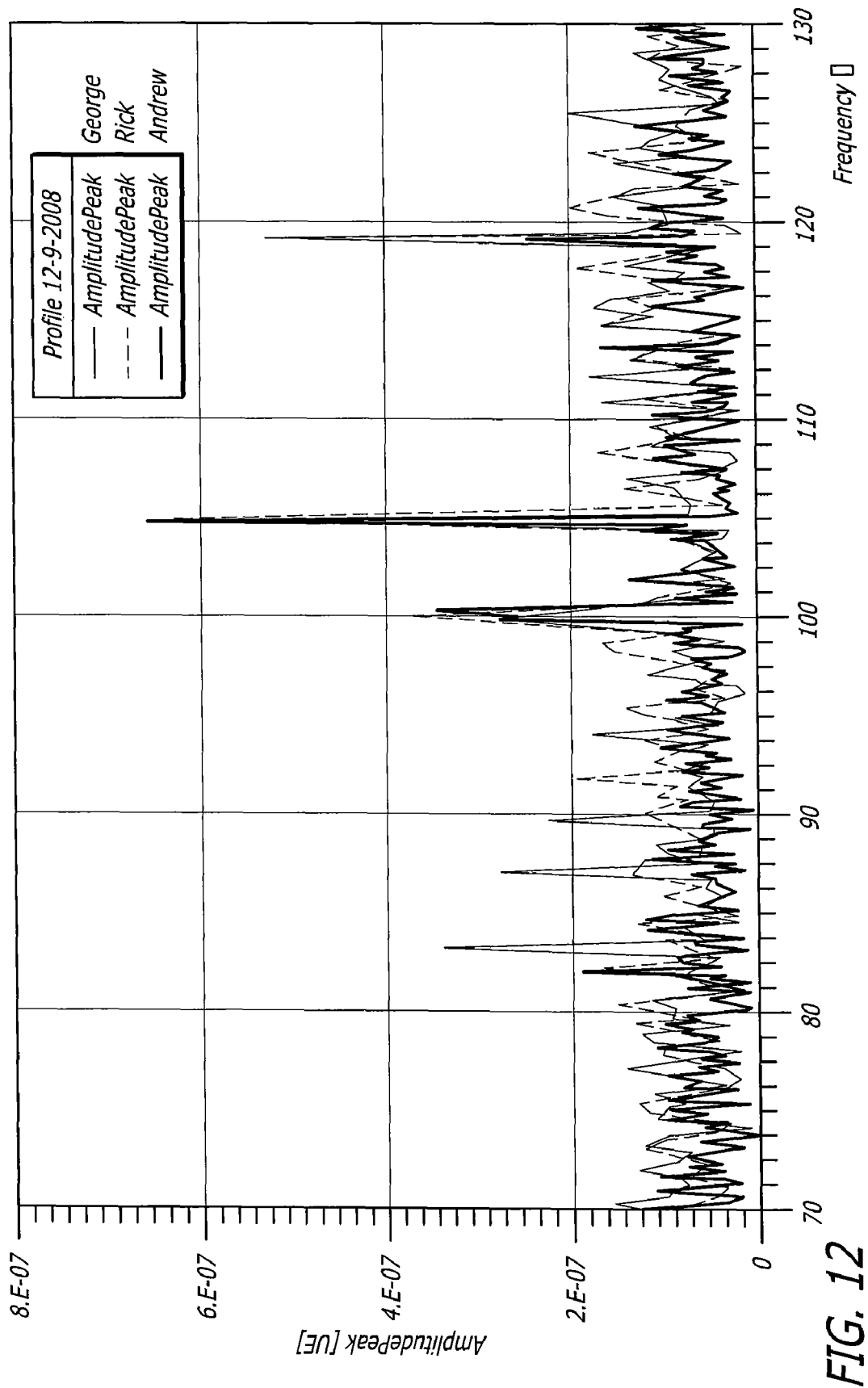
FIG. 12 depicts a graph illustrating the amplitude peaks over time for patients George, Rick and Andrew.
Figure 13:
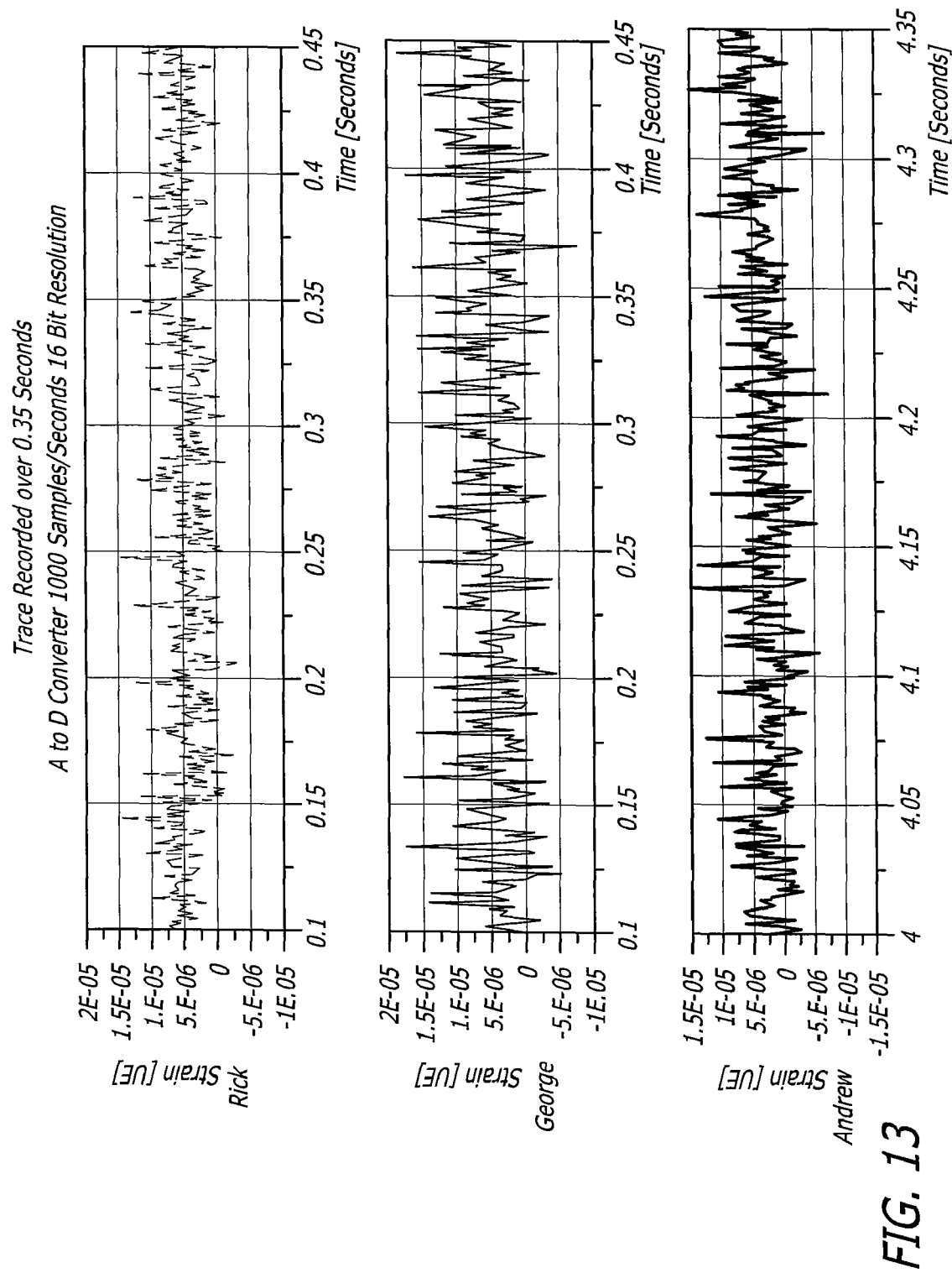
FIG. 13 depicts a graph illustrating strain over time for patients Rick, George and Andrew.

Experiments were conducted on individuals for the purpose of collecting ocular micro-tremor (OMT) data, analyzing the data, and demonstrating the correlation between OMT data and cognitive function (both normal and abnormal). As shown in FIG. 5, an OMT measurement apparatus in the form of safety glasses 20 includes a sensitive strain gauge sensor 22 attached to the glasses. The glasses were worn by subjects (Rick, George and Andrew) with closed eyelids for 10-15 seconds, and OMT data was formed by amplifying the signals received from the sensor, filtering the 60 Hz background noise, and displaying the signatures on a data logger trace. As shown in FIGS. 6-13, the analysis done was to display the data as a Fast Fourier transform (to display the content of signal information over a frequency domain), and a time based display, to show the more classical OMT signal, comprised of bursts and baseline areas. These curves show that individual data vary (all three men have no recorded case of cognitive impairments), but Rick is 56 years old and George is 67 years old, and both are clearly demarked from Andrew, who is 25 years old. As discussed earlier, Rick and George fall into a band of characteristics associated with advancing age. The data shown among the three subjects is consistent with observed slow down in cognitive processing with age. The dissimilarity is obvious within the Fast Fourier Transform display in frequency spectral content, as well as the time display curves. The present invention allows for various comparative and signal sampling methodologies to be used to contrast and compare individual OMT traces in all these domains to enhance the characteristics of groups. In that way, reference libraries of OMT data can be created that can be used by diagnostic laboratories to classify patients into cognitive categories, from normal to dysfunctional, with characteristics of various impediments (ADD, autistic, schizophrenic, etc.) as separate databases.

Figure 14:
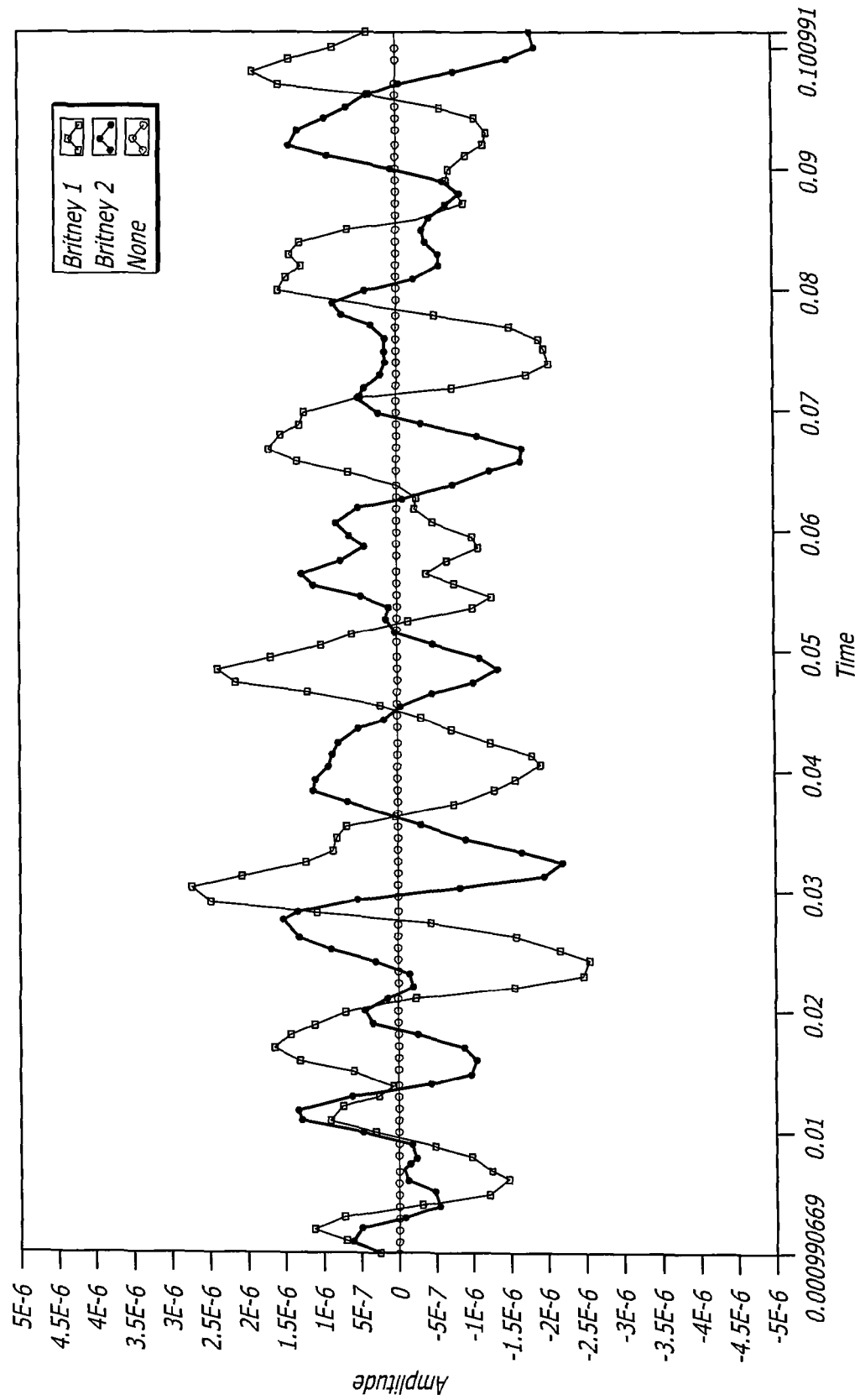
FIG. 14 depicts a graph illustrating amplitude over time for patient Britney.

As shown in FIG. 14, a patient named Britney was studied in a manner similar to that described for the patients in FIGS. 6-13. In this experiment, Britney wore the glasses (FIG. 5) on two occasions. Prior to testing, Britney had previously been diagnosed with moderate to severe ADHD by clinical psychologists. She takes prescription Adderal (extended time range Ritalin) to treat the symptoms and improve cognitive processing. Data was collected for Britney before taking her medication and about two hours after taking her medication. Referring to FIG. 14, Britney 1 is a chart of data collected before Britney took the medication and Britney 2 is a chart of data collected about two hours after Britney took her medication. The time scale (x-axis) is in increments of 0.01 sec. and has a duration of 0.1 sec. The amplitude (y-axis) is measured in micro volts. As can be seen from the data, the amplitude of the OMT ("eye wobble") is significantly smaller post-medication (Britney 2) versus pre-medication (Britney 1). Since eye motion is generally disruptive, the difference in the amount of motion detected from Britney 1 versus Britney 2 very likely correlates with usable levels of awareness. The OMT signature post-medication is approximately 1800 out of phase with the pre-medication signature, and it has shorter peak-to-peak periods. The data implies faster processing times after taking the medication, which may benefit those having ADHD, and appears more comparative to the normal patterns seen in prior subject traces. Further, increasing the dose of medication might show further benefits from the data. It is contemplated that a patient's medication could be fine tuned as the patient was being monitored in real time. For example, with respect to Britney, she could be monitored (using the system of FIG. 5) in real time as her medication was administered and varied. Over time, her medication could be optimized based on comparisons with the OMT data of normal patients collected and stored in a library. As the OMT data from Britney begins to fall within a range of normal OMT data residing in the library, then the medication level for Britney will have been optimized.

While particular forms of the present invention have been illustrated and described, various modifications can be made without departing from the spirit and scope of the invention. Accordingly, it is not intended that the invention be limited, except as by the appended claims.

What is claimed is:

1. A system for diagnosing Attention Deficit Hyperactivity Disorder (ADHD) in a patient, comprising:

a signal acquisition subsystem including a sensor for obtaining an ocular autonomic micro-tremor signal;

a signal processing subsystem for creating an ocular autonomic waveform signature from the acquired ocular autonomic micro-tremor signal;

a subsystem for accessing an ADHD reference library of ocular autonomic waveform signatures collected and measured from a plurality of previously diagnosed ADHD patients, wherein the signal acquisition subsystem creates the ADHD reference library by obtaining an ocular autonomic micro tremor signal from the plurality of previously diagnosed ADHD patients and the signal processing subsystem creates ocular autonomic waveform signatures from the acquired ocular autonomic micro-tremor signals of the plurality of previously diagnosed ADHD patients; and a correlation subsystem for comparing and correlating the patient's ocular autonomic waveform signature with the waveform signatures of the plurality of previously diagnosed ADHD patients in the ADHD reference library, whereby a match between the patient's ocular autonomic waveform signature and the waveform signatures of the previously diagnosed ADHD patients in the ADHD reference library provides a diagnosis of ADHD.

2. The system for diagnosing ADHD in the patient of claim 1, wherein the signal acquisition subsystem sensor is chosen from the group consisting of an optical sensor, a piezoelectric sensor, a strain gauge sensor, an accelerometer (sensor), a CW emitter/sensor, a pulsed light wave emitter sensor, and a sonic wave emitter/sensor, for discerning and measuring the autonomic micro motions and autonomic micro-tremors of the eye.

3. The system for diagnosing ADHD in the patient of claim 1, wherein the ocular autonomic waveform signature includes measuring and defining one or more parameters selected from the group consisting of: leading edge rise time slopes and trailing edge fall times slopes of repetitive sinusoidal components of the optical autonomic micro-tremor signal waveforms; midpoint and half-widths of repetitive sinusoidal components of the optical autonomic micro-tremor signal waveforms; separations between peak intervals; frequency of burst packages and waveform frequency of bursts and sinusoidal components; spindle associated with the waveforms; average and mean frequency of the waveform; time intervals between voids between the optical autonomic micro-tremor signal packets; and analyzing the mean amplitudes and extremes of the sinusoidal patterns and the collective bursts.

4. The system for diagnosing ADHD in the patient of claim 3, wherein transforms such as Fourier transforms are performed on the patient's ocular autonomic waveform signature.

5. The system for diagnosing ADHD in the patient of claim 1, further comprising a subsystem for generating a normal reference library of ocular micro-tremor waveforms signatures collected and measured from a plurality of cognitively normal patients, wherein the signal acquisition subsystem creates the normal reference library by obtaining an ocular autonomic micro tremor signal from the plurality of cognitively normal patients and the signal processing subsystem creates ocular autonomic waveform signatures from the acquired ocular autonomic micro-tremor signals of the plurality of cognitively normal patients without attention deficit diagnoses or other cognitive dysfunctions.

6. The system for diagnosing ADHD in the patient of claim 5, wherein the patient is diagnosed as cognitive dysfunctional when the patient's ocular autonomic waveform signature does not correlate with the normal reference library.

7. The system for diagnosing ADHD in the patient of claim 6, wherein the patient's ocular autonomic waveform signature is compared and contrasted to the normal reference library, a cognitive dysfunctional library and other categorized libraries of cognitive dysfunctional classes, including an ADD library and an ADHD library.

8. The system for diagnosing ADHD in the patient of claim 5, wherein the correlation subsystem is applied to the diagnosed ADHD patient both before onset of therapeutic interventions, and post therapy to compare and contrast benefits of given therapies toward producing ocular autonomic micro-tremor signatures more typically similar to those of cognitive normal populations represented by the normal reference library.

9. The system for diagnosing ADHD in the patient of claim 1, wherein the ocular autonomic micro tremor signals have an average frequency between:
a lower limit of approximately 30 Hz; and
an upper limit of approximately 100 Hz.

10. The system for diagnosing ADHD in the patient of claim 1, wherein the ocular autonomic micro tremor signals have an average amplitude between:
a lower limit of approximately 150 nm; and
an upper limit of approximately 2500 nm.

* * * * *